United States Patent
Chatzistergos et al.

(10) Patent No.: US 11,253,156 B2
(45) Date of Patent: Feb. 22, 2022

(54) ULTRASOUND IMAGING OF THE FOOT

(71) Applicant: Staffordshire University, Stafford (GB)

(72) Inventors: Panagiotis Chatzistergos, Stafford (GB); Roozbeh Naemi, Stafford (GB); Nachiappan Chockalingam, Stafford (GB)

(73) Assignee: Staffordshire University, Stafford (GB)

( * ) Notice: Subject to any disclaimer, the term of this patent is extended or adjusted under 35 U.S.C. 154(b) by 733 days.

(21) Appl. No.: 15/569,686

(22) PCT Filed: Apr. 25, 2016

(86) PCT No.: PCT/GB2016/051153
§ 371 (c)(1),
(2) Date: Oct. 26, 2017

(87) PCT Pub. No.: WO2016/174398
PCT Pub. Date: Nov. 3, 2016

(65) Prior Publication Data
US 2018/0116523 A1 May 3, 2018

(30) Foreign Application Priority Data
Apr. 27, 2015 (GB) .................................. 1507099

(51) Int. Cl.
*A61B 5/00* (2006.01)
*A61B 8/00* (2006.01)
(Continued)

(52) U.S. Cl.
CPC .......... *A61B 5/0053* (2013.01); *A61B 5/1036* (2013.01); *A61B 8/403* (2013.01);
(Continued)

(58) Field of Classification Search
None
See application file for complete search history.

(56) References Cited

U.S. PATENT DOCUMENTS 5,678,565 A 10/1997 Sarvazyan
2006/0103852 A1* 5/2006 Klaveness ............ A61B 5/1078
356/601
(Continued)

FOREIGN PATENT DOCUMENTS

CN 101569544 11/2009
CN 101569544 A * 11/2009 ............. A61B 5/441
(Continued)

OTHER PUBLICATIONS

English Translation of CN101569544A (Year: 2009).*
(Continued)

*Primary Examiner* — Joanne M Hoffman
(74) *Attorney, Agent, or Firm* — Bond, Schoeneck & King PLLC; Joseph M. Noto (57) ABSTRACT

The present invention relates to ultrasound imaging, and in particular to a device for imaging bodily tissue under load. The device has a platform (10), for at least partially supporting a part of the body (2), at least one ultrasound device (20) for imaging of the part of the body (2) in contact with the platform (10), and means (32) for measuring the pressure exerted on the platform (10).

24 Claims, 5 Drawing Sheets

(51) Int. Cl.
  *A61B 5/103* (2006.01)
  *A61B 8/08* (2006.01)
(52) U.S. Cl.
  CPC .......... *A61B 8/4272* (2013.01); *A61B 8/4416* (2013.01); *A61B 8/4461* (2013.01); *A61B 8/085* (2013.01); *A61B 8/0833* (2013.01); *A61B 8/0858* (2013.01); *A61B 8/42* (2013.01); *A61B 8/4455* (2013.01); *A61B 8/4477* (2013.01)

(56) References Cited

U.S. PATENT DOCUMENTS

| | | | |
|---|---|---|---|
| 2007/0038042 A1* | 2/2007 | Freeman | A61B 5/14552 600/310 |
| 2007/0244390 A1 | 10/2007 | Matsumura | |
| 2008/0306410 A1* | 12/2008 | Kalpaxis | A61B 5/1038 600/592 |
| 2009/0183388 A1 | 7/2009 | Miller et al. | |
| 2014/0121520 A1 | 5/2014 | Wang et al. | |
| 2015/0165690 A1* | 6/2015 | Tow | B29C 64/393 700/119 |
| 2015/0018679 A1 | 7/2015 | Endo | |
| 2015/0182158 A1* | 7/2015 | Ino | A61B 5/4827 600/557 |
| 2017/0027477 A1* | 2/2017 | Charles | A61B 5/1072 |

FOREIGN PATENT DOCUMENTS

| | | |
|---|---|---|
| RU | 2180517 C2 * | 3/2002 |
| WO | 0139668 | 6/2001 |
| WO | 2013130541 | 9/2013 |
| WO | 2016174398 | 11/2016 |

OTHER PUBLICATIONS

English Translation fo RU2180517C2 (Year: 2002).*
International Search Report and Written Opinion Form PCT/ISA/210, International Application No. PCT/GB2015/051153, pp. 1-14, International Filing Date Apr. 25, 2016, search report dated Oct. 31, 2017.
Trindade, et al., Development of a Wearable Ultrasonic Sensor and Method for Continuous Monitoring of Mechanical Properties of Plantar Soft Tissue for Diabetic Patients, 2014, IEEE International Ultrasonics Symposium Proceedings, pp. 2112-2115.
Bygrave, et al., The plantar tissue thickness in the foot: a new ultrasound technique for loadbearing measurements and a metatarsal head depth study, The Foot (1992) vol. 2, pp. 71-78, © 1992 Lonngman Group UK, Ltd.
Chatzistergos, et al., The relationship between the mechanical properties of heel-pad and common clinical measures associated with foot ulcers in patients with diabetes, 2014 Journal of Diabetes and Its Complications vol. 28, pp. 488-493, © 2014 Elsevier Inc.
International Search Report and Written Opinion Form PCT/ISA/210, International Application No. PCT/GB2015/051153, pp. 1-14, International Filing Date Apr. 25, 2016, search report dated May 8, 2016.
UK Intellectual Property Office Search Report, Application No. GB1507099.8, pp. 1-4, Filing Date Apr. 27, 2015, search report dated Sep. 24, 2015.

* cited by examiner

ULTRASOUND IMAGING OF THE FOOT

This application is a 371 application of International Patent Application No. PCT/GB2016/051153, filed Apr. 25, 2016, which claims the benefit of Great Britain Patent Application No. 1507099.8, filed Apr. 27, 2015, which are hereby incorporated by reference in their entirety.

The present invention relates to ultrasound imaging, and in particular to a device for imaging bodily tissue under load.

Bodily tissue can be examined using a process called palpation. In some cases palpation is a physical process performed by healthcare professionals or clinicians using their hands to examine a body or to assess characteristics of the bodily tissue. The experience and expertise of the clinician is essential in correctly interpreting sometimes subtle differences in the physical feel of the tissue in order to make a diagnosis.

Ultrasound palpation devices may also be used by clinicians to assess tissue. Such devices often comprise an ultrasound probe, which is manually applied to a region of tissue by a clinician. Information regarding the Young's modulus of the tissue can be obtained using such a device, and this data can be readily recorded and/or used to provide an image of the region being assessed. However, the expertise of a clinician is still often required for operation of the devices, in particular regarding correctly locating the region of tissue to be palpated and applying a suitable force. It is possible that the force applied to a patient's tissue using an ultrasound palpation device may result in damage to the tissue, particularly if the patient has decreased sensitivity in that region of tissue and is therefore not able to feel if the applied force is too large. Furthermore, the applied force can also distort the ultrasound images.

Despite these potential problems, it is beneficial for clinicians to be able to image different regions of a patient's body under load, because certain regions of tissue may cause pain or display other problems, such as abnormalities or pathologies, only when compressed. Imaging a patient's tissue under load allows the tissue function to be assessed.

One particular area of the body which can suffer problems under load is the sole of the foot. Tissue of the sole of the foot may become damaged, but this damage may not show itself when the foot is in an unloaded condition. It is widely believed that changes in the mechanical properties of plantar soft tissue are responsible for a number of pathologic and non-pathologic traumas such as ulcers and oedema. Patients suffering from diabetic foot may have decreased sensitivity in the sole of the foot, and therefore these patients may not feel tissue damage. In certain cases, tissue damage can worsen until amputation of the foot is necessary.

It is an object of the present invention to provide a device for obtaining information about tissue under load, which overcomes or substantially mitigates some, or all of the above mentioned and/or other disadvantages associated with conventional weight-bearing scans and palpation techniques.

According to a first aspect of the invention there is provided a device for measuring the properties of bodily tissue, the device comprising a platform for at least partially supporting a body or part of the body such that a load is applied by the body or body part to the platform, at least one ultrasound device, and means for measuring the pressure exerted by the body or body part on the platform, wherein, in use, ultrasound signals from said at least one ultrasound device radiate from or through the platform for imaging of the part of the body in contact with a major surface of the platform.

The diagnostic device is advantageous because it allows for both pressure measurement and ultrasound imaging of parts of the body under load. The weight of the body or the body part compresses structures and applies stress to help reveal certain pathology that may only be visible when the patient is in a weight-bearing or partial weight-bearing position. However, because the load is generally applied through the weight of the body or body part rather than by applied pressure from a third party, the chances of excess pressure being applied are minimised.

Furthermore, ultrasound imaging of parts of the body under load may provide data, and may enable reconstruction of tissue geometry, for example, under clinically relevant conditions. Imaging under controlled loading may also improve the reliability of the images.

The device may be suitable for measuring pressure and imaging of both humans and animals. The device may be used in both clinical and veterinary applications. The area of the platform may be between 0.01 $m^2$ and about 1 $m^2$ for humans, depending on the body parts to be measured, and up to about 10 $m^2$ for veterinary applications. The thickness of the platform may be between 1 mm and 100 mm. The platform may comprise a material that is sufficiently strong to bear the weight of a human or large animal.

The platform may be a rigid surface. The platform may comprise a material that does not exhibit significant deformation under the applied loads. The platform may be deformable by less than 10% of the original thickness. The material of the platform may be a polymer plastic or a fibre reinforced material.

Alternatively the platform may be a deformable platform. The platform may comprise a material that exhibits linear or non-linear mechanical deformation behaviour, and may comprise a material that exhibits high deformations under the applied loads. The platform may be deformable by up to 30%, up to 50%, up to 70% or up to 90% of the original thickness.

The platform may be flat when there is no force applied to the platform. If the platform is deformable, the platform may deform when a force is applied to the platform. The platform may have a smooth surface.

The platform may comprise a region of ultrasound-transparent material. The platform may comprise a plurality of regions of ultrasound-transparent material. The entire platform may comprise ultrasound-transparent material. By "ultrasound-transparent material" is meant a material with a sufficiently low-attenuation acoustic characteristic, eg a sufficiently low attenuation coefficient, that an effective image is obtained when ultrasound signals radiate through the platform. The ultrasound transparent material may be a solid gel, a silicone elastomer, a liquid pocket, a foam or another visco-elastic ultrasound transparent material. The ultrasound attenuation coefficient may be less than 2.0, less than 1.0 or less than 0.5 $dB \cdot MHz^{-1} \cdot cm^{-1}$ for example.

The device may comprise a base for resting on a support surface, eg the floor or ground, such that the device is self-supporting. The base may have a contact surface that contacts the support surface, in use. The contact surface may be substantially flat, or may be formed by a plurality of projections, eg legs, which contact the support surface. The platform orientated substantially parallel to the support surface and/or the contact surface of the base, in use, and hence the platform may be orientated substantially horizontally, in use. Alternatively, the platform may be provided in an inclined position, or adjustable to an inclined position, relative to the support surface and/or the contact surface of the base. For example, the inclined surface may be orientated at between 10° and 45°, or between 20° at 40°, relative to the support surface and/or the contact surface of the base, or relative to horizontal, in use. This may enable the measurement of tissue properties under shear loading.

The at least one ultrasound device may comprise a transmitter and a sensor. The transmitter and the sensor may be integrated within the same device. Alternatively, the transmitter and the sensor may be separate. The at least one ultrasound device may be substantially perpendicular to the platform, such that ultrasound signals are transmitted substantially perpendicular to a major surface of the platform. Additionally or alternatively, the at least one ultrasound device may be angularly adjustable such that the ultrasound signals may be transmitted at an angle relative to a major surface of the platform.

The at least one ultrasound device may be positioned beneath the platform, such that the platform lies between the ultrasound device and the part of the body that is placed on the platform.

The at least one ultrasound device may comprise a plurality of ultrasound transmitters and sensors. Additionally or alternatively, there may be provided a plurality of ultrasound devices. The plurality of ultrasound devices may be substantially perpendicular to a major surface of the platform such that ultrasound signals are transmitted substantially perpendicularly to the major surface of the platform.

There may be provided an array of ultrasound devices. The array may be a regular array or an irregular array. The array may be predetermined. The array may be variable. This feature is advantageous as it may be preferable in some cases to provide imaging over a large area, whereas in other cases a different array may be required to provide imaging over a specific, smaller area.

The plurality of ultrasound devices may be pen-shaped. The pen-shaped devices may have a cross-sectional area of less than 2 $cm^2$, or less than 1 $cm^2$. The pen-shaped devices may be generally cylindrical or prismatic in shape. The length of the pen-shaped devices may be between 1 and 10 cm. The pen-shaped devices may have a generally circular cross-section. The cross-section of each pen-shaped device may be shaped such that multiple devices are able to fit together in close proximity. The end of each pen-shaped device from which ultrasound signals are transmitted and/or received may include an ultrasound-transparent surface that is the size and shape of the cross-section of the pen-shaped device.

The plurality of pen-shaped ultrasound devices may be arranged in an array such that each pen-shaped device is upstanding and aligned parallel to the surrounding pen-shaped devices. The pen-shaped devices may be arranged such that each pen-shaped device is in contact with the surrounding pen-shaped devices. The pen-shaped devices may be arranged in sufficiently close proximity that the plurality of ends of the pen-shaped devices together provide a surface. The surface provided by the array of pen-shaped devices may be the platform of the diagnostic device. The surface may be flat and smooth when there is no force applied to the surface and may deform when a part of a body is placed on the surface.

A plurality of pen-shaped ultrasound devices is an advantageous feature as it may provide an increased sensitivity in ultrasound measurement. Furthermore, the feature of the cross-sectional surface of the array of pen-shaped devices providing the platform is advantageous because it removes the necessity for a further rigid, ultrasound transparent platform. Additionally, the movement of the pen-shaped devices may provide an opportunity to measure further parameters such as the shape and size of the body or part of the body.

The at least one ultrasound device may be movable. Additionally or alternatively, the means for measuring pressure may be movable. The at least one ultrasound device and/or means for measuring pressure may be movable in a direction generally perpendicular to a major surface of the platform, such that the distance between the at least one ultrasound device and/or the means for measuring pressure and the platform may be increased or decreased. The at least one ultrasound device and/or means for measuring pressure may be movable in a direction on a plane parallel to a major surface of the platform. The diagnostic device may comprise a movable formation. The diagnostic device may comprise a movable arm. The movable arm or movable formation may comprise an attachment means for attachment to the at least one ultrasound device and/or the means for measuring pressure. The movable arm or movable formation may facilitate movement of the ultrasound device and/or the means for measuring pressure.

A movable formation is advantageous as it allows different regions of tissue to be imaged or measured across the platform as required.

The means for measuring the pressure exerted by the person on the platform may be a pressure sensor. The pressure sensor may comprise a non-deformable material.

The pressure sensor may be positioned between the ultrasound device and the surface of the body which is placed on the platform. The pressure sensor may be placed on top of the platform. Alternatively, the pressure sensor may be placed beneath the at least one ultrasound device, at an opposing end of the device to the end which is closest to the platform.

The pressure sensor may comprise an ultrasound-transparent material.

The pressure sensor may measure the pressure across the entire surface of the part of the body placed on the platform. Alternatively, the pressure sensor may measure the pressure at different regions of the platform.

The pressure sensor may comprise a series of strips that are parallel to the platform surface. The length of the strips may be approximately equal to the length of the platform. The width of the strips may be less than 2 cm, less than 1 cm, or less than 0.5 cm. The series of strips may cover the entire width of the platform surface.

The pressure sensor may be removable from the platform. If the pressure sensor is not ultrasound-transparent, then it is advantageous that the pressure sensor is removable in order for ultrasound imaging to be performed when required.

If the platform comprises deformable material, then the means for measuring the pressure may comprise means for measuring deformations in the deformable material when a person stands on or places a part of a body on the platform. This feature is particularly advantageous in that it allows ultrasound imaging and pressure measurements to be performed simultaneously.

Additionally or alternatively, means for measuring pressure may comprise a force sensor. The force sensor may be positioned beneath the ultrasound device, such that when a part of the body is placed on the platform, a force is applied to the ultrasound device which is measured by the force sensor. This method is advantageous because it allows simultaneous ultrasound imaging and pressure measurement.

The device may comprise means for reconstruction of tissue geometry based on data received from the ultrasound sensor and/or the means for measuring pressure. This is advantageous as it can provide information regarding the tissue under different clinically relevant conditions.

The device may provide a means for calculating tissue properties based on data received from the ultrasound sensor and/or the means for measuring pressure.

The device may be provided as a diagnostic kiosk. The kiosk may be a standalone system. The kiosk may comprise the diagnostic device and a display means. The kiosk may also provide controls such as when to commence measurements. An advantage of the device being provided as a diagnostic kiosk is that it may be provided in a variety of settings such as a doctors' surgery, a pharmacy, a shop or a patient's home. The diagnostic kiosk may not require an expert clinician in operation.

The display means may be built-in or may be separate from the device. The display means may provide instructions to the user regarding the appropriate position on the platform to place a part of the body on, or the amount of force to apply to the platform. This feature is advantageous as it can provide instructions to the user to move the position of the part of the body in contact with the platform, in order to optimise the pressure and ultrasound measurements.

The display means may provide further information to the user, for example instructing the user to seek medical advice. This is particularly advantageous because the device may be used by a patient or operated by a non-specialist user in order to identify whether there may be a need for the patient to seek professional medical help. This is a helpful feature as advice can be provided to users in the time period between medical appointments.

The display means may provide information to a clinician, for example ultrasound images and pressure data. Information may be provided that will advise a clinician to repeat measurements or take further measurements, or to refer the patient to a different specialist.

A method of measuring tissue properties of a part of a body under load may comprise placing a part of the body on the platform; measuring the pressure distribution; and performing ultrasound imaging. This method is particularly advantageous in measuring tissue properties in the sole of a foot.

The pressure and ultrasound measurements may be static, i.e. the sole of the foot or any other part of the body is still when the measurements take place. The measurements may take place when a person is resting the sole of the foot or any other part of the body on the platform with no applied force. The measurements may take place when a person is standing with one foot on the platform and one foot elsewhere outside the device such that only part of the person's body weight is on the platform. The measurements may take place when a person is standing with both feet on the platform, such that the whole of the person's body weight is on the platform. The measurements may take place when a patient is sitting or lying on the platform. The measurements may take place when the patient is sitting on the platform with their back against a support. A combination of any of these weight-bearing measurements may be performed.

The pressure and ultrasound measurements may be dynamic. The measurements may take place when a person is walking on the platform. Alternatively, the platform may move or vibrate such that dynamic measurements may be performed without requiring the patient to lift up the foot or any other part of the body on the surface of the platform.

Ultrasound imaging and pressure measurements may be performed simultaneously. Alternatively, ultrasound imaging may precede or follow pressure measurements. Only one of ultrasound or pressure measurements may be required by the user.

Tissue properties may be determined based on ultrasound and/or pressure measurements. The properties may be calculated based on static and/or dynamic measurements. The properties may be calculated based on the tissue being under different loads. Any one of or any combination of the following properties may be measured based on the ultrasound and/or pressure measurements: tissue thickness, structural integrity, structural details, configuration of fatty cells, alignment of macro and micro chambers, internal deformation, energy absorption capacity, stiffness during loading, perfusion.

The tissue properties may be calculated using mathematical and reverse finite element modelling.

The measured tissue properties may be compared with thresholds. The thresholds may comprise previous measurements for the same person at a previous date. The thresholds may be predetermined thresholds. The predetermined thresholds may be thresholds for healthy tissue. The comparison between the measured tissue properties and the predetermined thresholds may be used for diagnosis.

The measured tissue properties may be presented on a display to inform the user or clinician.

The device may comprise means for prescription. The method may comprise prescribing an optimised insole. Mechanical properties of the insole may be prescribed using the measured tissue properties. The mechanical properties of an insole may be prescribed to decrease plantar soft tissue internal stress. The mechanical properties of an insole may be prescribed to decrease peak or average plantar pressure, plantar pressure-time integral, the rate plantar pressure is applied and/or plantar shear stress/load at a region of interest.

The diagnostic device may comprise means to calculate materials for an optimised insole. The diagnostic device may comprise means to calculate an optimised shape for an insole. A material may be selected from a database, where the selected material may have the closest mechanical properties to the mechanical properties identified, relative to other materials in the database.

Information regarding a prescribed insole may be communicated, for example to a clinician or an insole manufacturer. Data regarding the prescribed insole may be transmitted to a 3D printer. The information may be communicated using a display means. This is advantageous in a retail situation, as it may advise a user on the appropriate insole to purchase from a selection in a shop.

An insole may be manufactured which provides the required mechanical properties determined by the means for prescription. Manufacture of the insole may comprise cutting a flat insole from sheet of material which has the required mechanical properties. Alternatively, a contoured custom insole may be milled from a block of a selected material. Alternatively, a material with bespoke mechanical behaviour may be produced. A variable contoured insole may be printed from a 3D printer to match the required mechanical properties. 3D printing of bespoke insoles is advantageous as this method of manufacture has the ability to create a variety of different materials with different characteristics. These characteristics may include shore hardness, density, elasticity, viscosity, stress-strain relationship, etc.

The device may assist in selecting an appropriate insole from a range of insoles. The range of insoles provided may be ultrasound transparent. The range of insoles provided may comprise insoles of a variety of shapes and/or materials. The method of selecting an insole may comprise a user standing on the insole on the platform of the device; the pressure distribution may be measured and an ultrasound image may be obtained; tissue properties may be determined from the pressure and/or ultrasound data; tissue properties may be compared to thresholds to determine whether the insole is suitable. This method may be repeated with several insoles from the range and the appropriate insole may be determined.

This method is advantageous as it may provide information regarding whether a certain insole shape and/or material is likely to reduce pressure in required regions of the sole of the foot, to relieve or prevent certain symptoms.

Certain embodiments of the invention will be described in further detail below by way of example only with reference to the accompanying drawings, of which.

Figure 1:
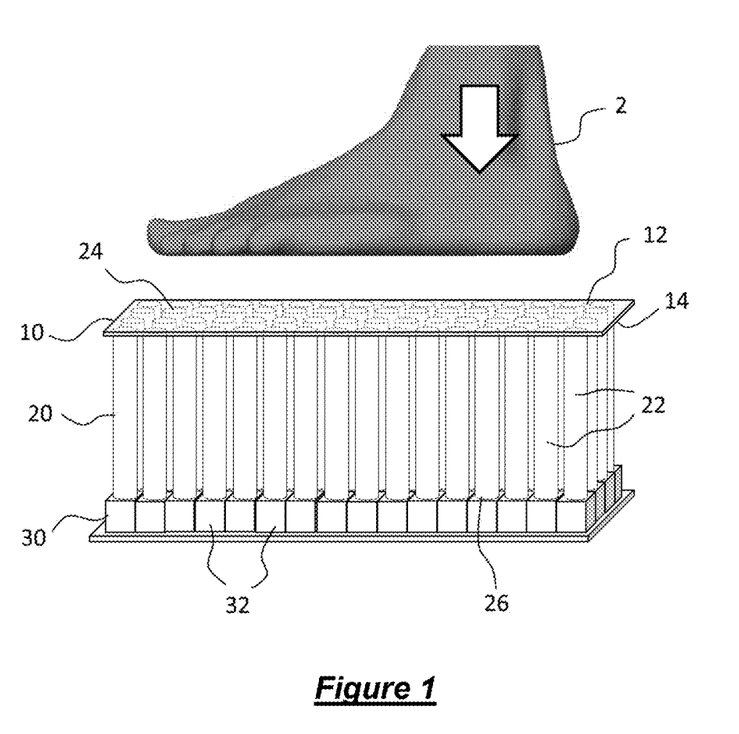
FIG. 1 is a three-dimensional view of a diagnostic device according to an example of the invention.

Referring firstly to FIG. 1, the diagnostic device comprises a platform 10 and an array of ultrasound devices 20 and a means for measuring pressure 30.

The platform 10 is generally rectangular in shape, but may be shaped differently to suit different applications. The thickness of the platform 10 is substantially constant across the surface of the platform.

The platform 10 is a thin film of an ultrasound-transparent material, with a first major surface 12 and a second major surface 14. The thickness of the platform 10 between the first major surface 12 and the second major surface 14 is less than 1 mm. In use, a body part of a user, for example the sole of a foot 2, contacts the first major surface 12 of the platform 10 and applies a load to the platform 10.

The array of ultrasound devices 20 shown in FIG. 1 comprises a plurality of pen-shaped devices 22. The pen-shaped devices 22 are generally cylindrical in shape, and are arranged such that the longitudinal axes of the devices are parallel with respect to each other. The diameter of each of the pen shaped devices 22 is less than 10 millimetres, for example 5 millimetres. The length of the pen-shaped devices 22 is of the order of several centimetres, for example 10 centimetres.

The circular cross-section of the pen-shaped devices 22 at an upper end 24 lies parallel to the second major surface 14 of the platform 10. The pen-shaped devices 22 are arranged such that the surfaces at the upper ends 24 of the devices 22 form a uniform two-dimensional array, in rows and columns, across the second, or bottom, major surface 14 of the platform 10.

The means for measuring pressure 30 comprises an array of force sensors 32. A force sensor 32 is positioned at the lower end 26 of each pen-shaped ultrasound device 22 such that a load applied to an upper end 24 of any pen-shaped ultrasound device 22 will be transmitted to an associated force sensor 32.

The platform 10 is deformable such that when a user places a body part in contact with the first major surface 12 of the platform 10, the thin film conforms to the body part. The deformation of the thin film allows different loads to be transmitted to different ultrasound devices 22 within the array 20, and thereby to different force sensors 32. A map of the pressure or load applied by the body part across the platform 10 can thus be generated. Simultaneously, the individual ultrasound devices 22 can perform measurements, through the ultrasound-transparent material of the platform 10, at the same points as the load measurements are taken. As a result, not only are the ultrasonic measurements taken under a load, but the specific load at each measurement point can also be determined.

Figure 2:
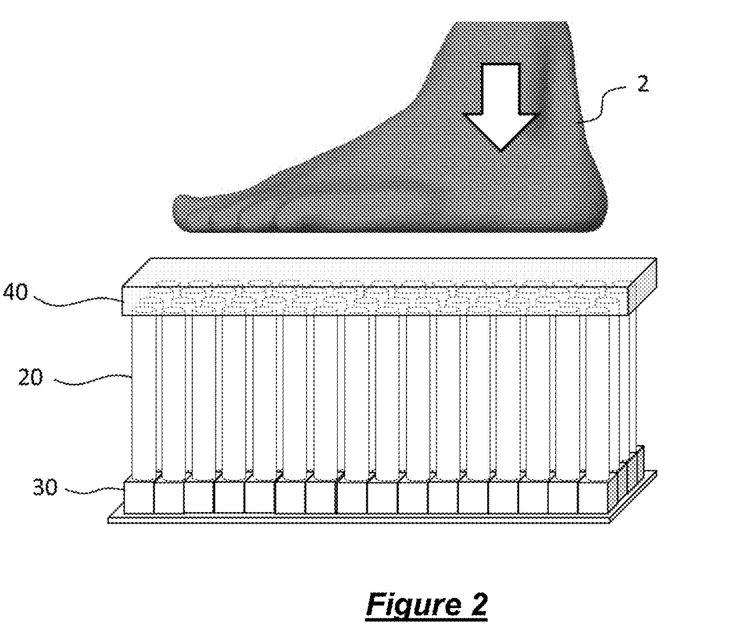
FIG. 2 is a three-dimensional view of a diagnostic device according to another example of the invention.

FIG. 2 shows another example of a diagnostic device, which comprises the array of ultrasound devices 20 and the means for measuring pressure 30, as described above in reference to FIG. 1. The example shown in FIG. 2 comprises a platform 40 which is formed from a soft ultrasound-transparent material. The platform 40 is of a thickness of the order of centimetres, for example 2 centimetres. The platform 40 is a deformable material, which is compressible under the weight of a foot in use. The platform may be deformable such that it substantially conforms in shape to the sole of the foot.

By replacing the thin film of the platform 10 from the first embodiment with a thicker platform 40 of soft deformable material, there is provided an additional means of determining the pressure distribution on the platform 40, by measuring the deformations of the soft deformable material when a load is applied by the body part on the platform.

Figure 3:
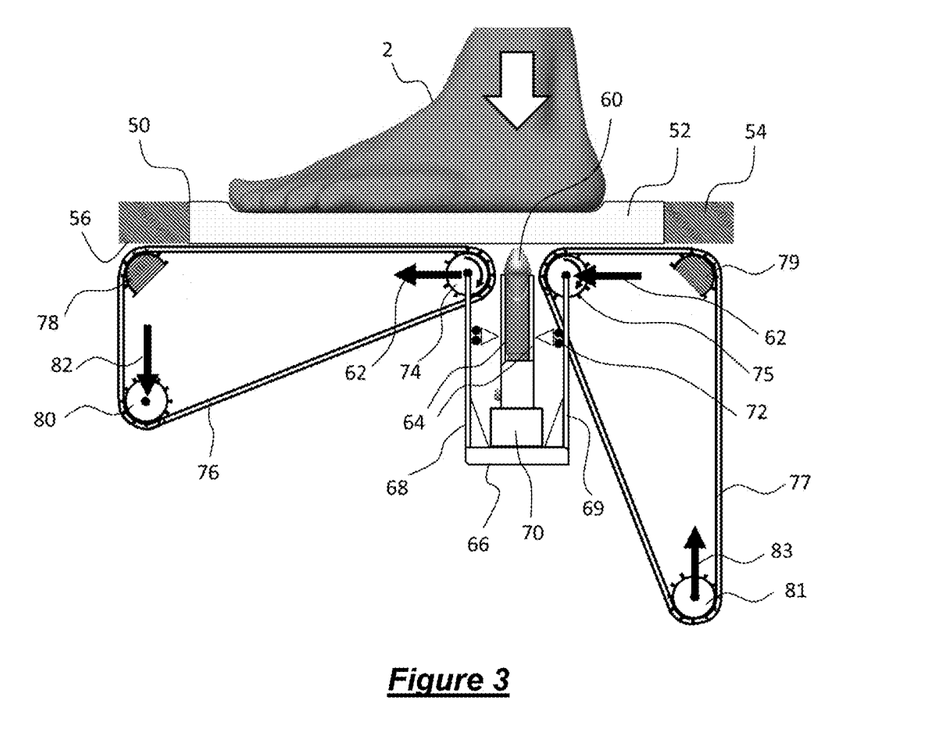
FIG. 3 is a schematic side view of a diagnostic device according to a third example of the invention.

FIG. 3 shows a third example of a diagnostic device according to the invention. The diagnostic device comprises a platform 50, an ultrasound device 60, and a force sensor 70.

The platform 50 comprises a region of deformable ultrasound-transparent material 52, and a rigid border 54 around the perimeter of the ultrasound-transparent material 52. The region of deformable ultrasound-transparent material 52 is deformable such that when a body part such as a foot 2 is placed on the platform 50, the material 52 is compressed under the weight of the foot 2, as shown in FIG. 3.

The ultrasound device 60 is an ultrasound probe, which is generally cylindrical in shape and approximately 5 centimetres in length. However, it should be understood that the ultrasound device may be any other type of clinical ultrasound probe, for example a probe with a linear array. The ultrasound device 60 is located beneath the platform 50, on the opposite side to that on which the foot 2 is placed in use. The ultrasound device 60 is movable on a plane parallel to the bottom major surface 56 of the platform 50, in the direction shown by the arrows 62. The ultrasound device 60 can be moved to different positions relative to the platform 50 to image different areas of the foot.

The ultrasound device 60 stands on a force sensor 70. Support members 64 are upstanding from the force sensor 70, and are arranged on either side of the ultrasound device 60, to provide support such that the ultrasound device is substantially perpendicular to the bottom major surface 56 of the platform 50.

The ultrasound device 60 and force sensor 70 are contained within a movable formation 66. The formation 66 comprises a base, from which the force sensor 70 and ultrasound device 60 are upstanding, walls 68, 69 and interior supports 72. The interior supports 72 contact the support members 64 and ensure that the ultrasound device 60 and force sensor remain in the desired position, substantially perpendicular to the platform 50, within the movable formation 66.

The walls 68, 69 are attached to the centres of wheels 74, 75 which are driven by a motor to allow movement of the movable formation 66 relative to the platform 50. A first loop 76 of a belt, towards the left of the device shown in FIG. 3, is provided around a first of these driven wheels 74, a first fixed corner piece 78 and a first movable wheel 80. A second loop 77 is similarly provided towards the right side around a second of the driven wheels 75, a second fixed corner piece 79 and a second movable wheel 81. The driven wheels 74, 75 rotate in a clockwise direction and move along their respective loop of the belt 76, 77 in the direction indicated by arrows 62, causing the movable formation 66 to move in that direction. The belt is fixed at the corner pieces 78, 79 while the further movable wheels 80 and 81 are provided to maintain tension in both loops 76, 77 of the belt. In particular, as the driven wheels 74, 75 move along the belt 76, 77 in the direction of arrows 62, the further movable wheels 80, 81 rotate clockwise and move in the direction indicated by arrows 82, 83.

Figure 4:
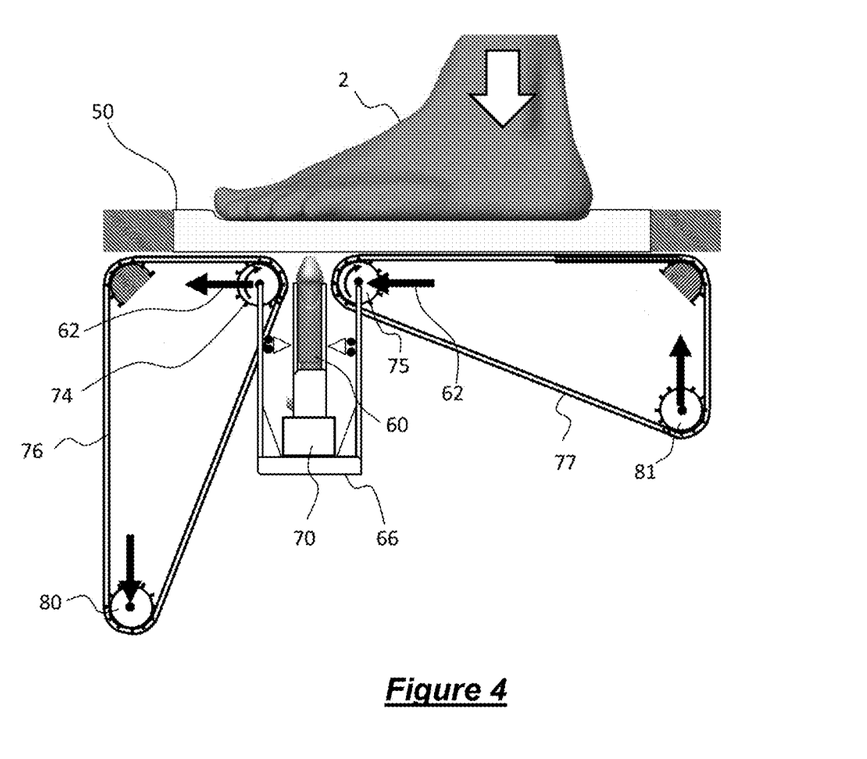
FIG. 4 is a schematic side view of a diagnostic device according to a third example of the invention in a different configuration from that of FIG. 3.

FIG. 4 shows the ultrasound device 60 of this example in another position, having moved in the direction of the arrows 62. As a result of the movement of the driven wheels 74, 75 to the left, the first movable wheel 80 has moved downwards, while the second movable wheel 81 has moved upwards to maintain tension in the belt 76, 77.

If the direction of motion imparted to the wheels 74, 75 is reversed such that the wheels 74, 75 rotate anticlockwise, the movable formation 66 will move in a direction opposite to that indicated by arrows 62, i.e. to the right as shown, and the first and second movable wheels 80, 81 will maintain tension by moving upwards and downwards respectively. In an alternative embodiment, wheels 74, 75 and corner pieces 78, 79 may be provided on a support plate beneath the platform.

Figure 5:
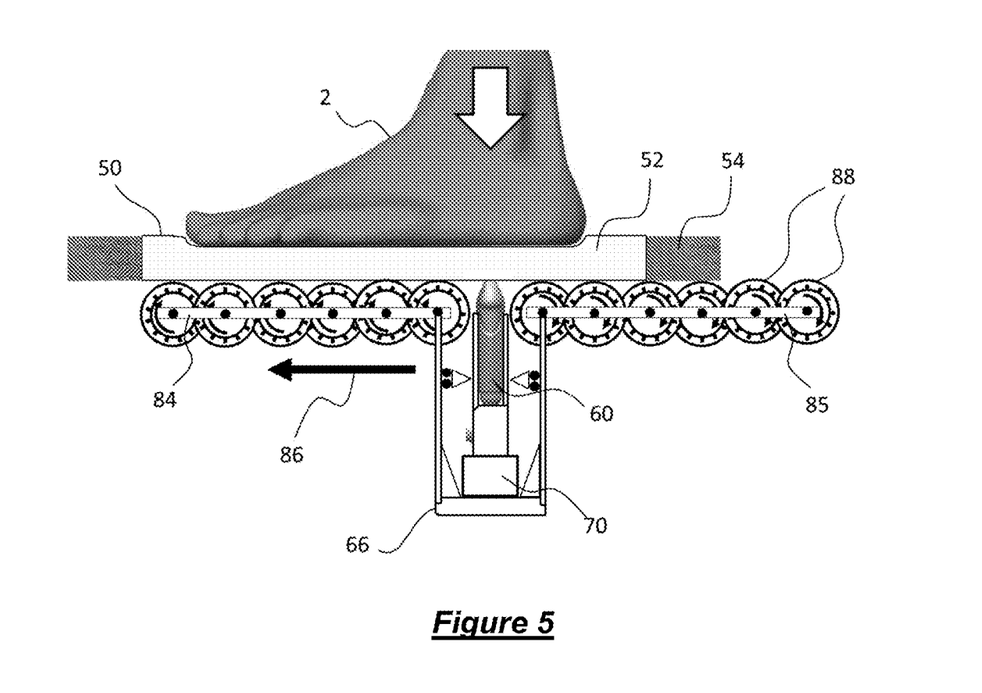
FIG. 5 is a schematic side view of a diagnostic device according to a fourth example of the invention.

FIG. 5 shows a diagnostic device according a fourth example of the invention. The device comprises a platform 50 comprising a deformable ultrasound-transparent material 52 with a rigid perimeter 54, as included in the embodiments shown in FIGS. 3 and 4. The device also comprises the movable formation 66 containing the ultrasound device 60 and force sensor 70. However, in the example of FIG. 5, the movable formation is fixed to bars 84, 85 and is movable in the direction indicated by arrow 86 through the clockwise rotation of wheels 88 arranged along the bars 84, 85. As before, the movable formation may be moved in a direction opposite to the arrow 86 simply by reversing the direction of rotation of wheels 88.

Figure 6:
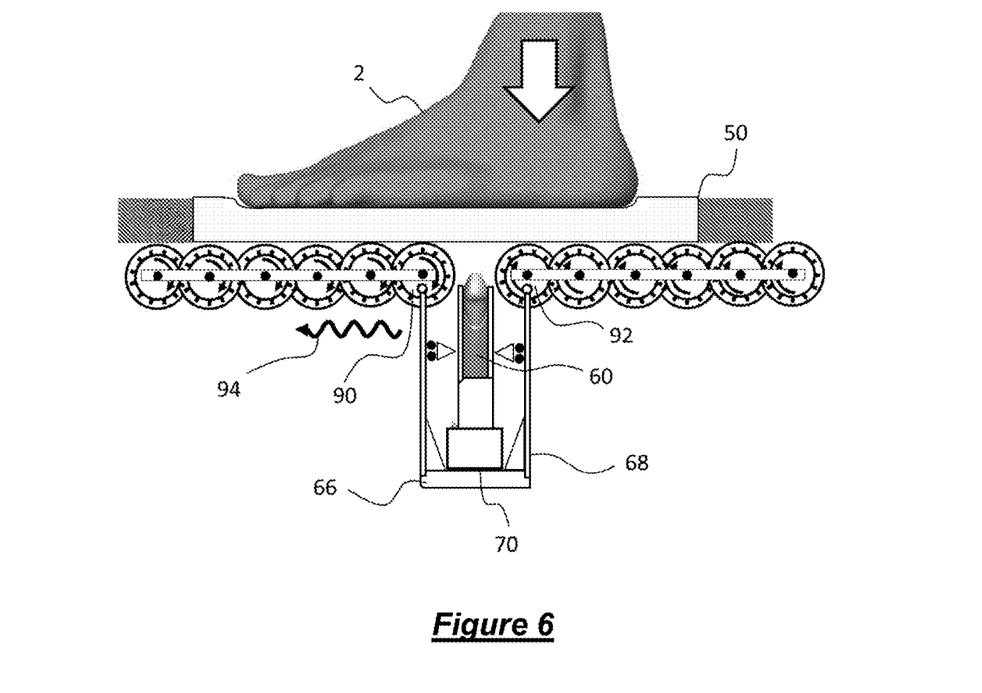
FIG. 6 is a schematic side view of a diagnostic device according to a fifth example of the invention.
Figure 7:
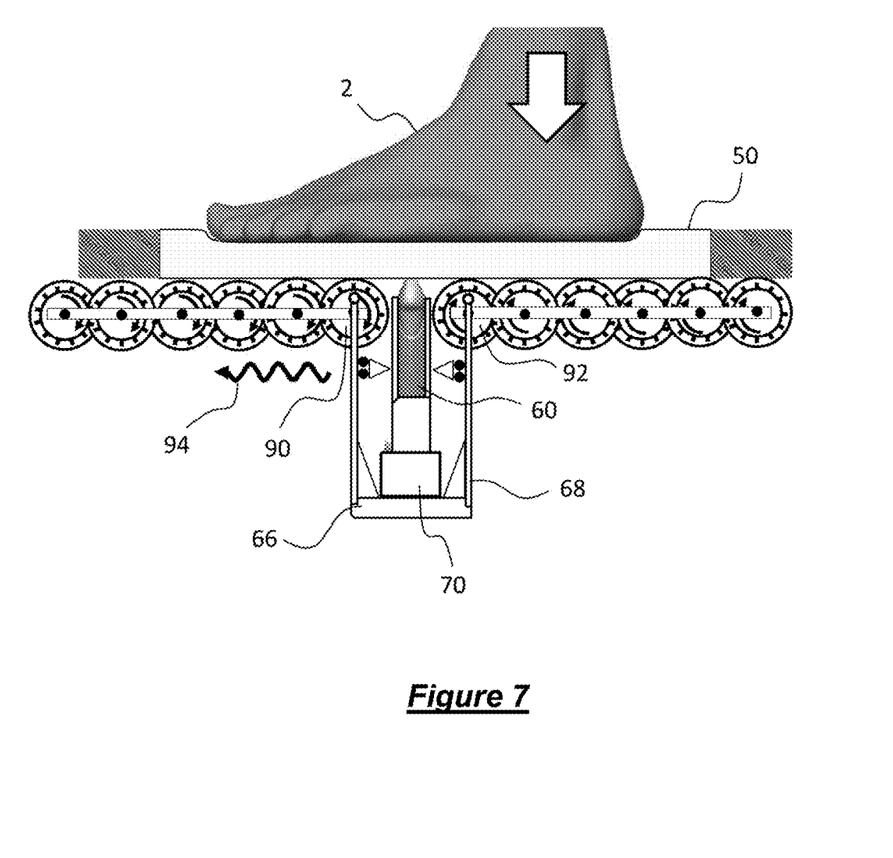
FIG. 7 is a schematic side view of a diagnostic device according to the fifth example of the invention in a different configuration from that of FIG. 6.

FIGS. 6 and 7 show another example that comprises a similar configuration to that shown in the example in FIG. 5. However, in this configuration each wall 68 of the movable formation 66 is affixed to a wheel 90, 92 at a point that is not the centre of the wheel. As a result, rotation of the wheels 90, 92 causes the movable formation to move in sinusoidal motion as indicated by the arrow 94. This provides a means of controllably varying the distance between the ultrasound device 60 and the sole of the foot during use. FIG. 6 shows the movable formation 66 in a position such that the ultrasound device 60 and force sensor 70 are at the greatest distance from the sole of the foot, and FIG. 7 shows the movable formation in a position such that the ultrasound device and force sensor are at the smallest distance from the platform. In this embodiment, ultrasound images are recorded only when the probe is at a minimum distance to the platform.

The sinusoidal motion of the movable formation significantly reduces the frictional forces between the ultrasound probe and the platform when the movable formation is moving to a different position beneath the platform. The deformable material of the platform may be urged against the ultrasound probe under weight-bearing conditions generating frictional forces during movement of the probe relative to the platform. In an alternative embodiment, the interface between the platform material and the ultrasound probe may be provided with an ultrasound-transparent gel. The gel may reduce the frictional forces between the deformable material of the platform and the ultrasound probe.

FIGS. 3 to 7 each show only one movable formation 66, containing an ultrasound device 60 and a force sensor 70, which moves in a direction indicated by the arrows in order to enable measurements along the length of the foot. However, in alternative embodiments, there may be a series of movable formations aligned parallel to each other, each containing an ultrasound device 60 and a force sensor 70, to also enable measurements across the width of the foot and provide measurements of a two-dimensional area of the sole of the foot. In other embodiments, the ultrasound probe may comprise a linear array of sensors. The linear array may extend across the majority of the width of the platform, such that as the ultrasound probe is moved along the length of the platform, measurements may be obtained over the area of the platform.

Alternatively, the devices in FIGS. 3 and 4 may be provided with movement axes along the axes of wheels 74, 75 and along fixed corner pieces 78, 79 as shown. The device may then comprise a mechanism such that movement of the movable formation 66 is enabled along these axes to obtain ultrasound and force sensor measurements across the width of the foot when the foot is in a position as shown in the examples in FIGS. 3 and 4.

The examples above are given only to help explain the nature of the invention, and are not intended to limit the protection sought. Features described in relation to one example may be applied, where suitable, to another example. In particular, the fixing of the movable formation 66 to an off-centre point on the wheels described in relation to FIGS. 6 and 7 could similarly be applied to the example shown in FIGS. 3 to 5 to provide a similar sinusoidal movement of the ultrasound device 60.

Although the illustrated examples described above refer in general to measurements of the sole of a foot, it will be readily understood that the specific devices would equally function as described to take measurements of other body parts located on the platforms 10, 40, 50.

Included within each of the embodiments of the diagnostic device, but not shown in FIGS. 1 to 7, are means for calculating tissue properties based on data received from the ultrasound device and/or the force sensor. Additionally, there may be means to display the calculated tissue properties, or memory storage on which to store data regarding the properties and measurements obtained from the ultrasound device and force sensor.

The invention claimed is:

1. A device for measuring the properties of bodily tissue, the device comprising an ultrasound-transparent platform for at least partially supporting a body or part of the body such that a load is applied by the body or body part to the platform, a formation moveable along the underside of the platform by a drive mechanism and containing at least one ultrasound device, and a pressure sensor which measures the pressure exerted by the body or body part on the platform, wherein, in use the at least one ultrasound device is in contact with the surface of the platform, ultrasound signals from said at least one ultrasound device radiate from or through the platform for imaging of the part of the body in contact with a surface of the platform.

2. A device for measuring the properties of bodily tissue, the device comprising a platform for at least partially supporting a body or part of the body such that a load is applied by the body or body part to the platform, a plurality of adjacent stationary ultrasound devices each having a distal end in contact with an underside surface of the platform and a pressure sensor which measures the pressure exerted by the body or body part on the platform, wherein, in use, ultrasound signals from said plurality of ultrasound devices radiate from or through the platform for simultaneously imaging the entire part of the body in contact with the surface of the platform.

3. A device as claimed in claim 2, wherein the ultrasound devices are arranged in an array such that each ultrasound device is upstanding and aligned parallel to each surrounding ultrasound device.

4. A device as claimed in claim 3 wherein the ultrasound devices are arranged in sufficiently close proximity that an end of each ultrasound device of the plurality of ultrasound devices together form a base.

5. A device as claimed in claim 1, wherein the drive mechanism is a roller system or a pulley system.

6. A device as claimed in claim 5, wherein the at least one ultrasound device is movable in a direction perpendicular to the surface of the platform.

7. A device as claimed in claim 5, wherein the at least one ultrasound device is movable in a direction parallel to the surface of the platform.

8. A device as claimed in claim 1, wherein the at least one ultrasound device is substantially perpendicular to the surface of the platform, in order that ultrasound signals are transmitted substantially perpendicular to the surface of the platform in use.

9. A device as claimed in claim 1, wherein the at least one ultrasound device is angularly adjustable in order that ultrasound signal may be transmitted at an oblique angle relative to the surface of the platform.

10. A device as claimed in claim 1, wherein the pressure sensor is located, in use, between the surface of the platform and the body or body part which is placed on the platform.

11. A device as claimed in claim 10, wherein the pressure sensor is ultrasound transparent.

12. A device as claimed in claim 10, wherein the pressure sensor is removable from the device.

13. A device as claimed in claim 1, wherein the pressure sensor is positioned at an opposing end of the at least one ultrasound device to the surface of the platform.

14. A kiosk comprising a device according to claim 1, and display for providing information and/or instructions regarding the device and data received from the at least one ultrasound sensor and/or pressure sensor.

15. A system for assessing the suitability of an insole, the system comprising a device according to claim 1 and a three-dimensional replica of an insole formed from an ultrasound-transparent material.

16. A method for measuring the properties of bodily tissue, comprising the placing a foot on the platform of the device as claimed in claim 1, determining a pressure distribution indicative of the pressure between the platform and a surface of the sole of the foot, imaging the foot by the at least one ultrasound device and manufacturing an insole based on bodily tissue properties.

17. The method of claim 16, further comprising calculating properties of the bodily tissue based on pressure and/or ultrasound measurements.

18. The method of claim 17, further comprising the step of comparing the calculated properties of the bodily tissue to predetermined thresholds.

19. The method of claim 18, further comprising the step of providing an indication of the presence or absence of one or more possible medical conditions or abnormalities based on the comparison.

20. A method for assessing the suitability of an insole, comprising providing the system according to claim 15, placing the sole of a foot on a replica insole on the platform of the measuring device, measuring with the pressure sensor of the measuring device the pressure distribution of the sole of the foot on the replica insole, imaging the sole of the foot with the at least one ultrasound device of the system and accepting or rejecting the replica insole based upon the measured pressure distribution and/or ultrasound imaging.

21. The method as claimed in claim 20, further comprising the steps of determining tissue properties from the measured pressure distribution and/or ultrasound image, comparing the tissue properties to predetermined thresholds, accepting the insole if the tissue properties are below the predetermined threshold, or rejecting the insole and repeating the method with one or more different replica insoles if the tissue properties are above the predetermined threshold.

22. The method according to claim 21, wherein data from the assessment of each replica insole is stored to permit a comparison between insoles of a variety of shapes and/or materials.

23. The method according to claim 16, wherein the pressure distribution is determined and the bodily tissue is imaged while the part of the body is moved onto and off the platform to provide dynamic measurements.

24. The method according to claim 16, wherein the platform vibrates while the pressure distribution is determined and the bodily tissue is imaged to provide dynamic measurements.

* * * * *